(12) United States Patent
Lange

(10) Patent No.: US 7,130,037 B1
(45) Date of Patent: Oct. 31, 2006

(54) SYSTEMS FOR INSPECTING WAFERS AND RETICLES WITH INCREASED RESOLUTION

(75) Inventor: Steven R. Lange, Alamo, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 164 days.

(21) Appl. No.: 10/725,744

(22) Filed: Dec. 2, 2003

Related U.S. Application Data

(60) Provisional application No. 60/438,977, filed on Jan. 9, 2003.

(51) Int. Cl.
*G01N 21/00* (2006.01)

(52) U.S. Cl. ................... 356/237.2; 356/237.5

(58) Field of Classification Search ............. None
See application file for complete search history.

(56) References Cited

U.S. PATENT DOCUMENTS

| | | | | |
|---|---|---|---|---|
| 4,049,350 | A | * | 9/1977 | Bruck .................... 356/30 |
| 4,346,164 | A | | 8/1982 | Tabarelli et al. |
| 4,509,852 | A | | 4/1985 | Tabarelli et al. |
| 4,544,626 | A | | 10/1985 | Sullivan |
| 4,898,804 | A | | 2/1990 | Rauschenbach et al. |
| 5,004,307 | A | | 4/1991 | Kino et al. |
| 5,023,424 | A | | 6/1991 | Vaught |
| 5,040,020 | A | | 8/1991 | Rauschenbach et al. |
| 5,121,256 | A | | 6/1992 | Corle et al. |
| 5,208,648 | A | * | 5/1993 | Batchelder et al. ...... 356/237.1 |
| 5,298,939 | A | | 3/1994 | Swanson et al. |
| 5,444,529 | A | * | 8/1995 | Tateiwa .................... 356/337 |
| 5,610,683 | A | | 3/1997 | Takahashi |
| 5,825,043 | A | | 10/1998 | Suwa |
| 5,900,354 | A | | 5/1999 | Batchelder |
| 6,191,429 | B1 | | 2/2001 | Suwa |
| 6,493,156 | B1 | | 12/2002 | Oh et al. |
| 6,606,150 | B1 | * | 8/2003 | Bickert et al. ............. 356/124 |

(Continued)

FOREIGN PATENT DOCUMENTS

WO 00/23840 4/2000

(Continued)

OTHER PUBLICATIONS

Love et al., "Microscope Projection Photolithography for Rapid Prototyping of Masters with Micron-Scale Features for Use in Soft Lithography," Langmuir, vol. 17, 2001, pp. 6005-6012.

(Continued)

*Primary Examiner*—Michael P. Stafira
(74) *Attorney, Agent, or Firm*—Ann Marie Mewherter; Daffer McDaniel, LLP

(57) ABSTRACT

Various inspection and review systems for wafers or reticles are provided. One system includes an optical component configured to project light onto a specimen during inspection or review. The system also includes a liquid disposed between and in contact with surfaces of the optical component and the specimen. The liquid does not permanently alter properties of the optical component or the specimen. Preferably, the presence of the liquid between the optical component and the specimen increases the resolution of the inspection or review system. Another system includes an inspection or review subsystem configured to project light through an optical component, a liquid, and onto a specimen. The liquid contacts the optical component and the specimen. This system also includes a processing subsystem configured to remove the liquid from the specimen after inspection or review. In some embodiments, the processing subsystem is configured to clean the specimen after inspection or review.

20 Claims, 7 Drawing Sheets

U.S. PATENT DOCUMENTS 6,819,427 B1 * 11/2004 Subramanian et al. ...... 356/445
6,870,610 B1 * 3/2005 Struckhoff et al. ....... 356/237.1

FOREIGN PATENT DOCUMENTS

WO 02/063613 8/2002

OTHER PUBLICATIONS

Genut et al., "Chemically Assisted Laser Removal of Photoresist and Particles from Semiconductor Wafers," presented at the 28th Annual Meeting of the Fine Particle Society, 1988, 11 pages.

* cited by examiner

SYSTEMS FOR INSPECTING WAFERS AND RETICLES WITH INCREASED RESOLUTION

PRIORITY CLAIM

This application claims priority to U.S. Provisional Application No. 60/438,977 entitled "Systems for Inspecting Wafers and Reticles with Increased Resolution," filed Jan. 9, 2003.

BACKGROUND OF THE INVENTION

1. Field of the Invention

This invention generally relates to optical systems for inspecting wafers or reticles with increased resolution. Certain embodiments relate to inspection systems that include a liquid disposed between an optical component of the system and a specimen.

2. Description of the Related Art

As the dimensions of transistors and related structures on semiconductor wafers continue to shrink, the need to detect and identify defects on the wafers and on the reticles used in the lithography process to fabricate the wafers continues to increase. The size of these defects follows the size of the structures on the wafers with a defect about half the minimum dimension on the wafers being considered a "killer" defect that can cause the device to fail. The current minimum dimension on semiconductor devices is about 100 nm with research and development work being conducted on 70 and 50 nm structure sizes. Wafer yield is a function of the number and type of these killer defects, and for more efficient processing and profitability, the number of defects needs to be minimized by first identifying their existence on the wafer and then correcting the root cause. Thus, the detection of defects on both the wafer and reticle is a critical function in current semiconductor fabrication facilities (fabs).

Current fabs utilize various optical inspection tools to locate these defects and classify them into categories, which are related to their root cause. As the size of the defects decreases, the need for higher sensitivity inspection and review tools follows. Generally, sensitivity is related to optical resolution for techniques, which use microscopes to examine the wafers and reticles for defects. Resolution is defined as: Resolution=$\lambda/n(NA)$, where $\lambda$ is the wavelength, n is the index of refraction, and NA is the numerical aperture of the optical system at the object. The NA of a typical inspection or review optical tool is currently in the range of 0.90 to 0.95 with a maximum theoretical value of 1.0, so little opportunity exists to increase resolution with this variable. The cost of increasing the NA beyond 0.90 is very expensive due to the difficulty in controlling optical aberrations. The minimum wavelength of current inspection and review tools is in the range of 248 to 266 nm, but the lack of inexpensive continuous sources with wavelengths below this variable is too expensive to consider. The final variable is the index of refraction, which can be a fluid disposed between the surface of the object to be inspected and the last optical surface of the inspection optical system. The higher the index, the better the resolution and smaller defects can be detected, and the increased resolution aids in their classification.

Therefore, it would be advantageous to increase the resolution of optical systems by increasing the index of refraction of the fluid between the object's surface and the last surface of the lens thereby increasing the system's sensitivity without increasing the NA and/or decreasing the wavelength of illumination thereby alleviating the design, manufacture, and test difficulties associated with high-resolution optical systems in addition to reducing the cost of such optical systems.

SUMMARY OF THE INVENTION

The present invention pertains to an optical inspection and review system capable of higher resolution and sensitivity to the detection and characterization of defects on semiconductor surfaces and reticle surfaces. One aspect of the invention that contributes to increased resolution is the use of a fluid with an index of refraction higher then air being located between the surface under examination and the last surface of the optical system conducting the examination of the surface. In one embodiment, the fluid is water with an index of refraction in the deep ultra violet spectrum of about 1.35, which increases the resolution by a factor of about 1.35. This resolution can be equivalent to an effective wavelength of about 197 nm with a light source of 266 nm. Other embodiments include oils and fluids that can have an index of refraction in the vicinity of 1.5, which emulates a wavelength of about 177 nm.

One aspect of the fluid is that it is inert and does not affect the surface under examination in any adverse manner, is relatively transparent at the wavelengths at which the inspection or review system operates, is void of any foreign matter which will scatter light, is compatible with the inspection lens surface, and is completely removed from the surface when the inspection has been completed.

Another aspect of the present invention is relative motion between the surface under examination and the optical system conducting the examination to cover the area to be inspected or reviewed. Another aspect of the present invention is that the fluid has a surface tension low enough to completely fill the wafer or reticle structures without air bubbles or voids in the presence of the relative motion.

Another aspect of the present invention is a mechanism for introducing and removing the fluid between the surface under examination and the inspection and/or review optical system during the relative motion. Several embodiments are described to effectively control the fluid and its properties during inspection or review.

These and other features and advantages of the present invention will be presented in more detail in the following description of the invention and the accompanying figures, which illustrate by way of example the principles of the invention.

BRIEF DESCRIPTION OF THE DRAWINGS

Other objects and advantages of the invention will become apparent upon reading the following detailed description and upon reference to the accompanying drawings in which.

Figure 1:
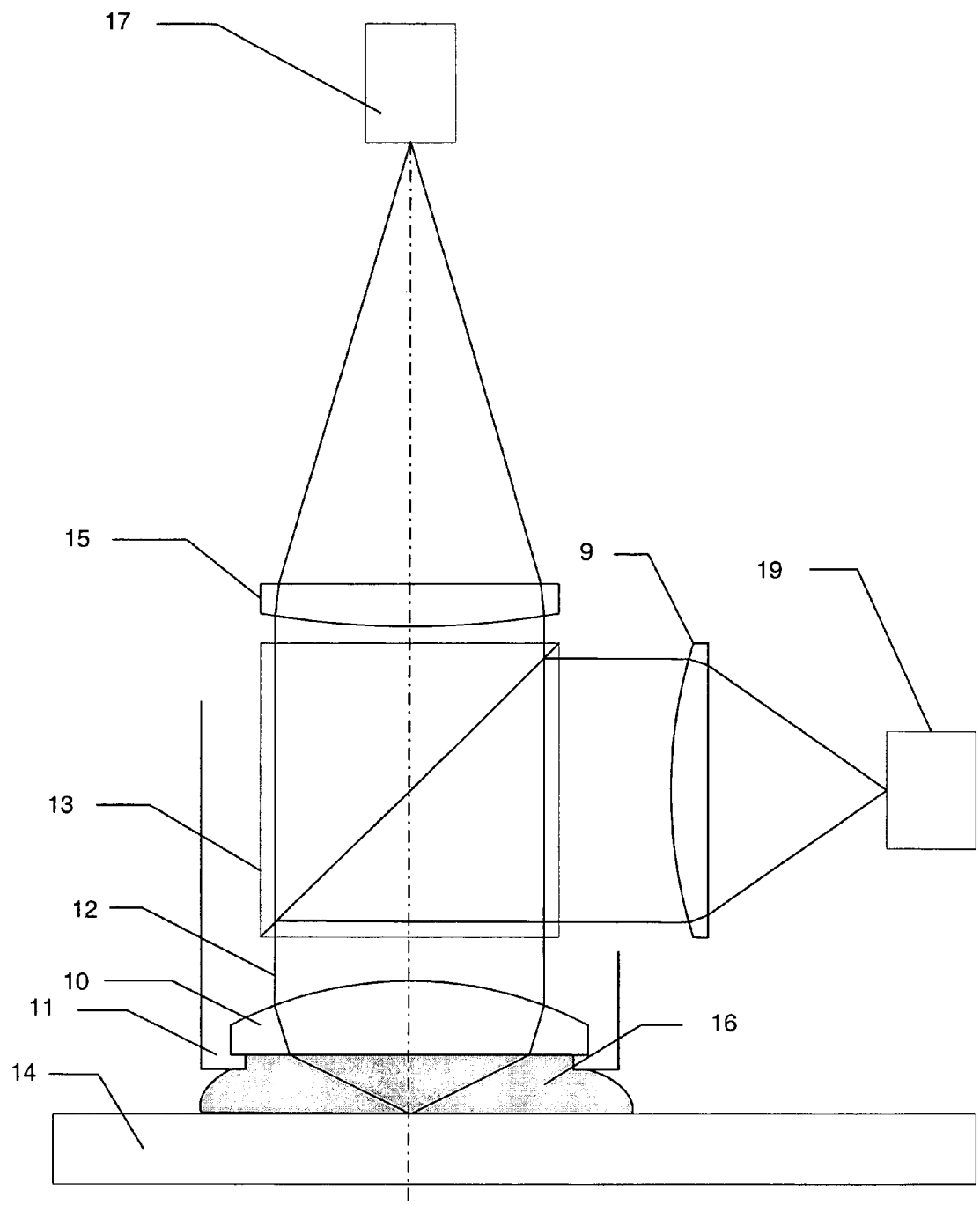
FIG. 1 is a schematic diagram illustrating a partial cross-sectional view of an embodiment of an inspection or review system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following description generally relates to systems for inspecting wafers or reticles with increased resolution. As used herein, the term "specimen" is generally used to refer to either a wafer or a reticle. The term "wafer" generally refers to substrates formed of a semiconductor or a non-semiconductor material. Examples of such a semiconductor or a non-semiconductor material include, but are not limited to, monocrystalline silicon, gallium arsenide, and indium phosphide. Such substrates may be commonly found and/or processed in semiconductor fabrication facilities. The term "inspection" refers to finding defects on the wafer or reticle. The term "review" refers to collecting light from the wafer or reticle to determine the type of defect or its characteristics.

Turning now to the drawings, it is noted that FIGS. 1–8 are not drawn to scale. It is also noted that FIGS. 1–8 are not drawn to the same scale. Elements of FIGS. 1–8 that may be similarly configured have been indicated with the same reference numerals. However, it is to be understood that elements of different figures that are indicated with the same reference numerals do not have to be similarly configured.

FIG. 1 illustrates an embodiment of an inspection or review system. The system includes optical component 10. Optical component 10 is configured to project light 12 onto specimen 14 from source 19 during inspection or review of the specimen. In some embodiments, optical component 10 may be configured to focus collimated light onto the specimen forming an illumination spot from source 19 such as a laser through optics 9 and beamsplitter 13. Although optics 9 is shown in FIG. 1 to include only one lens, it is to be understood that optics 9 may include more than one optical component. In another embodiment, optical component 10 may illuminate an area on specimen 14 from an extended source 19 such as an arc lamp. In one embodiment, optical component 10 may be an objective lens. In other embodiments, the optical component may be a relay lens, a prism, a window, a condenser lens, or any other refractive or reflective optical component known in the art. Optical component 10 may also be configured to collect light returned from specimen 14 and to transfer that light onto detection device 17 through beamsplitter 13 and lens system 15. Although lens system 15 is shown to include one lens, it is to be understood that the lens system may include one or more optical components. In addition, the optical component may be configured such that the system performs bright field inspection or review of the specimen. "Bright field" generally refers to a collection geometry configured to collect specularly reflected light from a specimen. A bright field collection geometry may have any angle of incidence although typically it may have an angle of incidence normal to the specimen plane. Such an optical component may include, for instance, a relatively high numerical aperture (NA) objective lens. The optical component, however, may have any NA.

The inspection or review system may include one or more additional components (not shown) coupled to optical component 10. Examples of such additional components include, but are not limited to, additional light sources, homogenizers, apertures, filters, additional beamsplitters, reflective components such as folding mirrors, additional lenses, telescopes, and additional detectors. Such components are known in the art and will not be discussed further herein. Such additional components may be configured with respect to optical component 10 such that the inspection or review system performs bright field inspection or review of specimen 14. Alternatively, the additional components may be configured with respect to optical component 10 such that the inspection or review system performs dark field inspection or review of specimen 14. "Dark field" generally refers to an optical configuration in which no specular light is reflected into the lens collection numerical aperture. In other embodiments, a combination of dark field and bright field can be collected by the optical system for dark field and bright field inspection or review of the specimen.

In other embodiments, the additional optical components may be configured with respect to optical component 10 such that the inspection system detects light transmitted by the specimen. In such embodiments, optical component 10 may or may not be configured to collect light returned from the specimen. Such an inspection system may be configured for inspection of specimen that have at least some transparent, or semi-transparent, portions such as a reticle.

In additional embodiments, the inspection or review system may be configured as a confocal optical system. In general, a confocal optical system includes one or more point light sources that are focused as a spot onto a specimen. Light reflected, scattered, or transmitted from the specimen is imaged onto one or more point detectors or detector arrays. The image may be obtained by scanning. The point illumination of a confocal configuration provides higher resolution than a conventional optical configuration. In addition, a confocal system can be used to generated three-dimensional images of a specimen by superimposing image data obtained at different focal depths. One example of a confocal optical microscope is illustrated in U.S. Pat. No. 6,248,988 B1 to Krantz, and is incorporated by reference as if fully set forth herein. Each of the above configurations are generally known in the art, and therefore will not be described further herein.

The inspection or review system also includes liquid 16 disposed between optical component 10 and specimen 14. Liquid 16 is in contact with a surface of optical component 10 and a surface of specimen 14. Therefore, if optical component 10 is a lens, the optical component may be configured as an immersion lens. In an embodiment, the liquid occupies approximately an entire volume between the surfaces of optical component 10 and specimen 14 out to lens cell 11. For example, the liquid may be selected based on the surface tension of the optical component and the surface tension of an upper layer on the specimen. Surface tension is a measurement of surface energy. Surface tension is the property due to molecular forces by which liquids through contraction of the surface tend to bring a contained volume onto a shape having the least surface area. Therefore, surface tension is indicative of the wettability of the surfaces of the optical component and the upper layer of the specimen. The higher the surface energy of a solid relative to a surface tension of a liquid, the better its wettability. As a general rule, a solid may be wetted by a liquid when the surface energy of the solid is about 10 dynes/cm greater than the surface tension of a liquid.

In one embodiment, the liquid is water. However, if the surface of the optical component or the surface of the specimen is hydrophobic due to its surface tension, the liquid may include a wetting agent. A "wetting agent" as used herein is defined as a liquid that can be added to another liquid to improve the wettability of the other liquid with respect to a specific solid. For example, if the surface of the specimen is hydrophobic, an appropriate wetting agent may be a polymeric surfactant or another surfactant that has a hydrophobic portion and a hydrophilic portion. In this manner, the hydrophobic portion may be attracted to the surface of the specimen while the hydrophilic portion may be repelled by the surface of the specimen. Other aqueous fluids will also be repelled by the surface of the specimen. In this manner, the surfactant may be selectively adsorbed from the liquid onto the surface of the specimen. The surfactant may thereby form a monolayer on the surface of the specimen with the hydrophilic portion of the surfactant extending away from the surface of the specimen. In this manner, the surfactant may form a molecularly oriented monolayer on the surface of the specimen. The surface of the specimen with the monolayer of the surfactant formed thereon may, therefore, be essentially hydrophilic. In a similar manner, the properties of the optical component or the specimen may be temporarily altered if the surfaces are hydrophilic and the liquid is non-aqueous. The wetting agent may be added to the liquid in relatively small amounts. For example, in one embodiment, a substantial portion of the liquid may be water. In some embodiments, the liquid may be 80%, 85%, 90%, 95%, 97%, or 99% water by volume. The other portion of the liquid may be the wetting agent or surfactant.

In other embodiments, the liquid may include a non-aqueous liquid such as an organic liquid. One example of an organic liquid is oil. The liquid may also include one or more liquids, which may or may not include a wetting agent. For example, the liquid may include water and an organic liquid such as oil. The liquid, and if included, the wetting agent, should be selected such that the liquid is compatible with other chemicals used for processing the specimen. For example, in the case of semiconductor or reticle manufacturing, the liquid and all of its components should be compatible with other chemicals used to process wafers or reticles.

Figure 2:
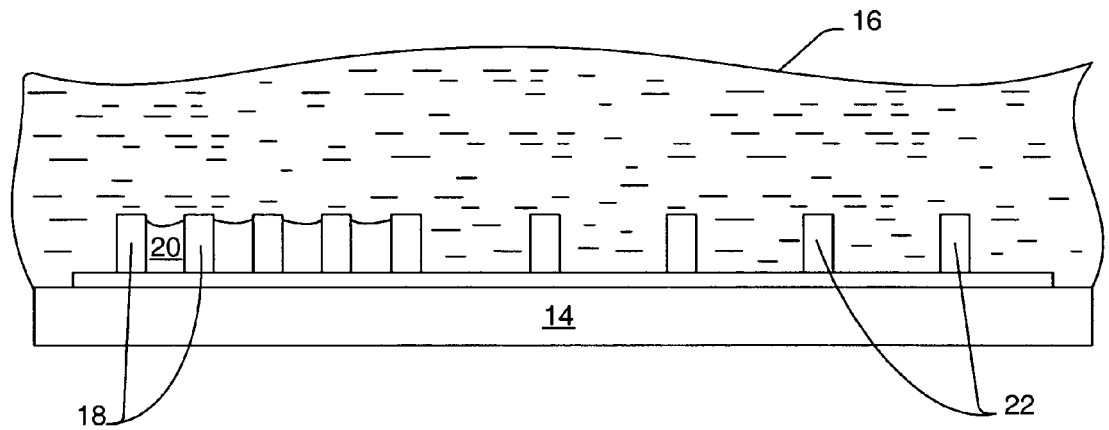
FIGS. 2 and 3 are schematic diagrams illustrating partial cross-sectional views of a liquid disposed upon a specimen.
Figure 3:
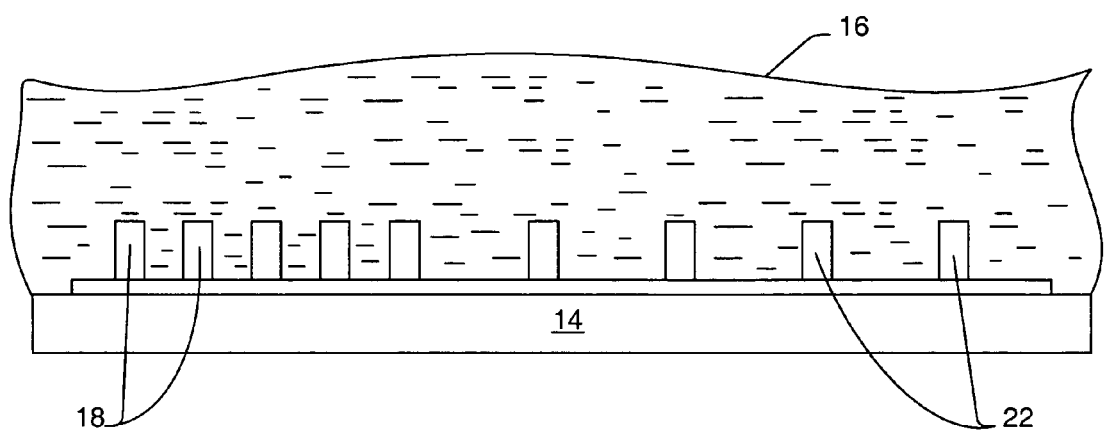

In addition, surface features, structures, or roughness on the optical component and the specimen may determine if air is present between the optical component and the specimen. For example, as shown in FIG. 2, features 18 formed on specimen 14 are relatively close together and have a high aspect ratio between the depth and the height of the structures. In this manner, the surface tension of the liquid may prevent the liquid from filling spaces between features 18. As such, air 20 or another gas may be present between features 18. In contrast, features 22 are relatively far apart and have a low aspect ratio between the depth and the height of the structures. Therefore, the liquid may substantially fill spaces between features 22 even though the liquid does not fill spaces between features 18. Since the aspect ratio of spaces between surface features, structures or roughness on the optical component and the specimen may not be altered in most cases, the liquid may be selected to have a surface tension as described above to ensure that no air is present between the surface features, the structures, or the roughness. For example, as the aspect ratio of features on the surface of the specimen increases, the surface tension of the liquid may be decreased to increase the volume of liquid between the features. In addition, as the aspect ratio of features on the surface of the specimen increases, the time between immersion of the specimen and commencement of inspection or review may be increased to allow the fluid to "settle" by gravitational flow into the high aspect ratio spaces. For example, if a period of time is allowed to pass after immersion of the specimen in a liquid, the liquid may fill the spaces between features 18 in addition to the spaces between features 22 as shown in FIG. 3.

By selecting a liquid as described above and/or allowing the fluid adequate time to flow into spaces in the specimen and/or the optical component, air, other gases, or voids may not be present between the surfaces of optical component 10 and specimen 14. In this manner, the air, other gases, or voids may not interfere with inspection or review of the specimen. For example, if bubbles are present between the surfaces of optical component 10 and specimen 14, the bubbles may alter the path of the light and may be mistakenly identified as defects on the specimen. In addition, the liquid should be selected such that the liquid does not scatter light projected onto the specimen by the optical component, light returned from the specimen, or light transmitted by the specimen in some cases such as reticle inspection. For example, the liquid should be substantially free of particulate matter or other solid contamination. In some embodiments, the liquid can be filtered to "ultra-pure" standards prior to immersing the specimen in the liquid. The liquid can be filtered using, for example, filtration processes that are known in the art of semiconductor manufacturing, which require such "ultra-pure" standards. Furthermore, the liquid should be selected such that the liquid provides relatively high transmission at the wavelength or wavelengths of light used by the inspection or review system.

The presence of liquid 16 between optical component 10 and specimen 14 advantageously increases the resolution of the inspection or review system. For example, in one embodiment, the liquid is selected such that the liquid has an index of refraction (n) that is approximately equal to the index of refraction (n) of optical component 10. In this embodiment, the presence of liquid between the optical component and the specimen increases the optical resolution of the inspection or review system by a factor (n). n may be approximately 1.35 for common liquids such as water. Therefore, in terms of resolution, the increase in optical resolution is approximately equivalent to an increase in optical resolution that would result from decreasing the wavelength of the light from about 266 nm to about 197 nm, or from about 230 nm to about 173 nm. In this manner, the inspection or review system may have an equivalent wavelength of about 173 mm, which is lower than most of the currently available shorter wavelength ArF excimer lasers at 193 nm. Consequently, the systems described herein provide increased optical resolution for inspection, and in some cases review, without the extremely high cost associated with either shorter wavelengths or higher NAs.

In some embodiments, the liquid may be selected such that the inspection or review system has a resolution equivalent to that of a lithography exposure system even if the inspection or review system does not have the same illumination wavelength or numerical aperture as the exposure system. Such an inspection or review system may be configured to simulate other optical conditions of the lithography system. In this manner, the inspection or review system may be configured to inspect a specimen such as a reticle under exposure conditions of the lithography system. Such an inspection or review system may also be configured to form an aerial image of the reticle. Therefore, the inspection or review system may be used to identify printable defects on the reticle.

Furthermore, the inspection roadmap is reaching a blockade at wavelengths under 266 nm (for wafer inspection) and possibly 196 nm (for reticle inspection) due to acceptable illumination sources. It is believed that no other potential resolution improvement mechanism is known or available other than e-beam inspection, which may also be reaching a blockade due to the speed limitations of such inspection systems. Therefore, the inspection or review systems described herein may provide the only solution for meeting the resolution requirements for inspection and review.

The liquid may also be selected to have an index of refraction that is different than an index of refraction of an upper layer formed on the specimen. For example, in the case of a wafer, the upper layer may be a resist, a conductive layer, or a dielectric layer. In these examples, the liquid may have a different index of refraction than the resist, the conductive layer, or the dielectric layer. The upper layer may also include a patterned layer and exposed portions of a layer underlying the patterned layer. In this example, the liquid may have an index of refraction different than the index of refraction of the patterned layer. In some cases, the liquid may also have an index of refraction different than the index of refraction of the underlying layer.

The liquid, preferably, does not alter properties of the optical component or properties of the specimen. For example, the liquid is selected such that the liquid does not alter dimensions, shape, roughness, or optical properties of the optical components or specimen. For example, the liquid may be selected such that the liquid is compatible with the surface chemistry of the lens. In addition, the liquid may be selected such that the liquid is substantially chemically inert with respect to the materials of the specimen that are exposed to the liquid. As described above, however, the liquid may temporarily alter properties such as wettability of the optical component or the specimen.

Figure 4:
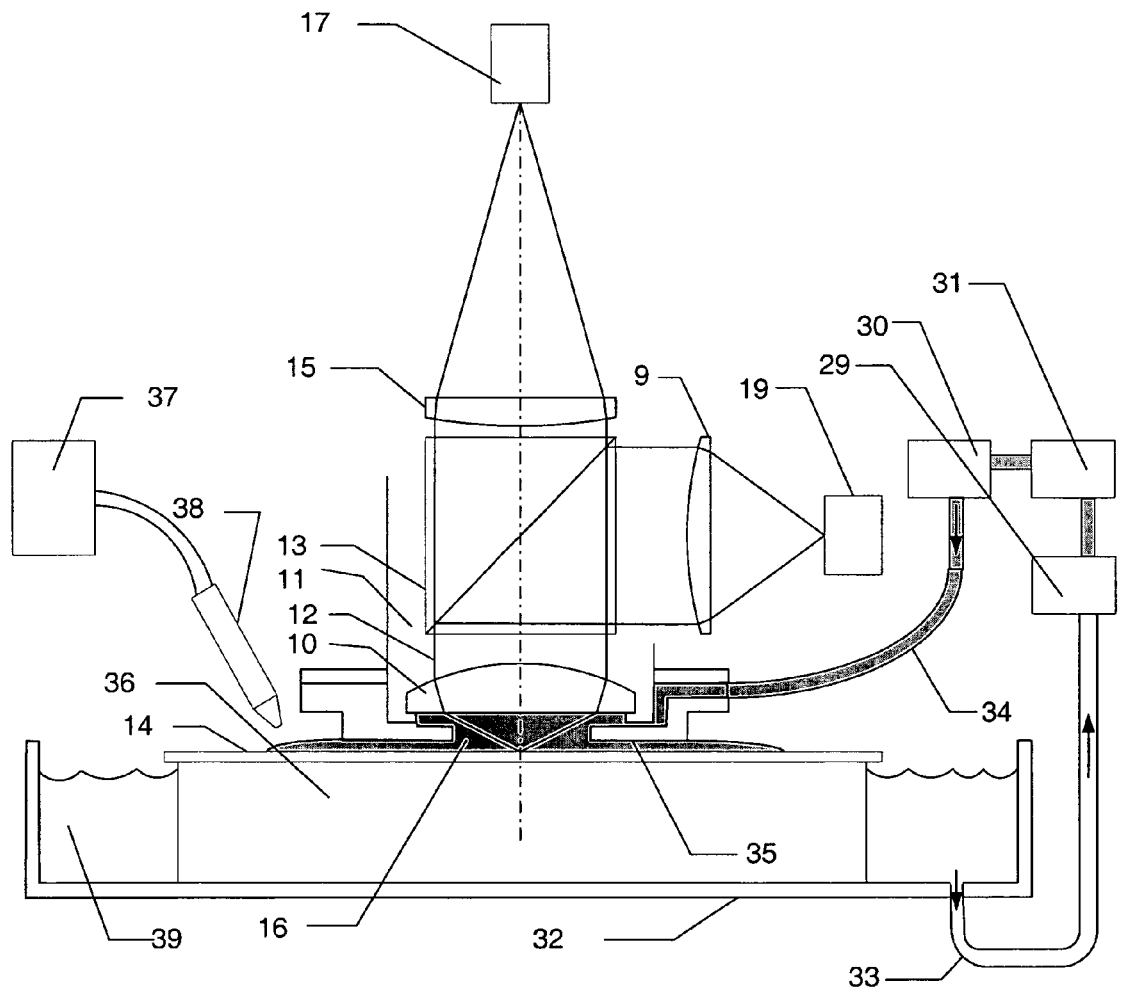
FIG. 4 is a schematic diagram illustrating a partial cross-sectional view of a system for disposing an immersion liquid between the inspection or review system and the surface under examination.

The inspection system may also include a containment system. The containment system may be configured to contain the liquid and the specimen immersed in the liquid. One example of a containment system is illustrated in FIG. 4. As shown in FIG. 4, specimen 14 is disposed upon object 36 which may be a vacuum chuck or other suitable support for a semiconductor wafer or an edge support suitable for a reticle. Immersion liquid 16 is contained in reservoir 39 with the containment system 32 holding the liquid. The liquid is pumped via path 33 using pump 29 through filter system 31, and temperature control system 30 and by path 34 to baffle structure 35 around the bottom surface of optical component 10. Immersion liquid 16 is forced through the opening in baffle structure 35 into the volume between the optical component and the specimen 14 and out of the space between baffle 35 and specimen 14. Residual immersion liquid can be blown off of specimen 14 using compressed air or other gasses from source 37 through one or more nozzles 38, where the liquid returns to reservoir 39. Therefore, the system is configured to generate flow of the liquid between the surfaces of the optical component and the specimen during inspection.

The containment system and its various components may be formed of a variety of materials. The material of which the containment system is formed is preferably compatible with the liquid. For example, the material of the containment system should be substantially inert with respect to the liquid. In addition, the material of the containment system should contain relatively low levels of extractable ions such that the containment system will not introduce ionic contamination to the liquid or the specimen. Some examples of appropriate materials for the containment system may include stainless steel, fluoropolymers such as polytetrafluoroethylene (PTFE) and polyvinylidene fluoride, and other polymers such as polyethylene and polypropylene.

Figure 5:
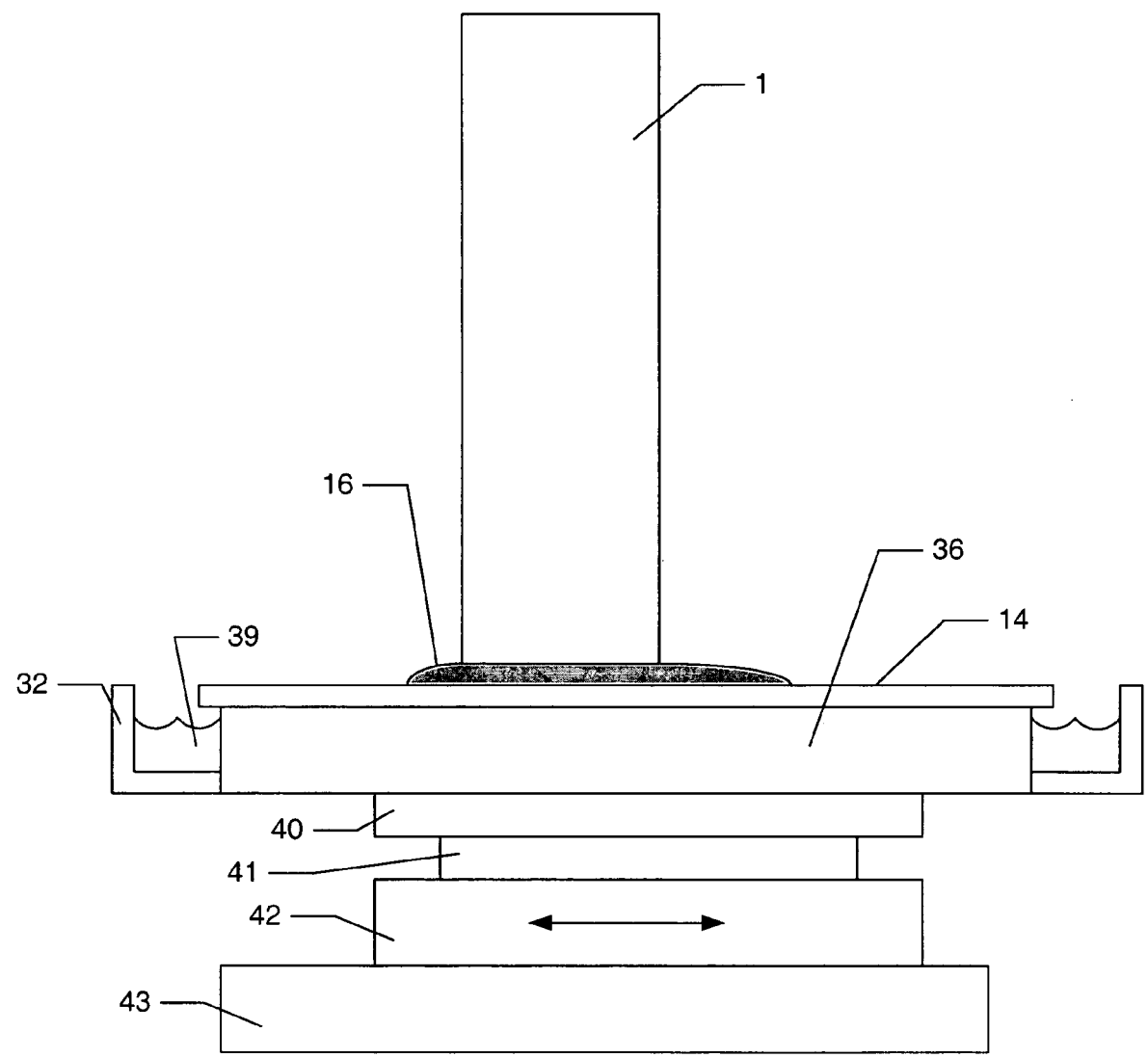
FIG. 5 is a schematic diagram illustrating a partial cross-sectional view of a system for transporting and aligning the surface under examination and the inspection or review system while containing the immersion liquid.

FIG. 5 illustrates containment system 32 attached to a support for the surface under examination using a fluid handling system as described for FIG. 4. A vacuum chuck may be used for supporting semiconductor wafers. Support 36 is attached to a stack of motion control and alignment stages. These stages are used to align the semiconductor wafer to the coordinate system of inspection or review system 1 and to move the surface under system 1 to cover all or most of the surface area. The stage system can include z-stage 40 for focusing, theta-stage 41 for rotation of the sample relative to the inspection or review system 1, x-stage 42 and y-stage 43 for translation of the specimen relative to the inspection or review system. The order of the stages can be switched, but the intent is that they provide relative motion between specimen 14 under examination or review and inspection or review system 1. Immersion liquid 16 is contained in reservoir 39 and is carried along with the motion of support 36 during the motions to inspect the surface.

Figure 6:
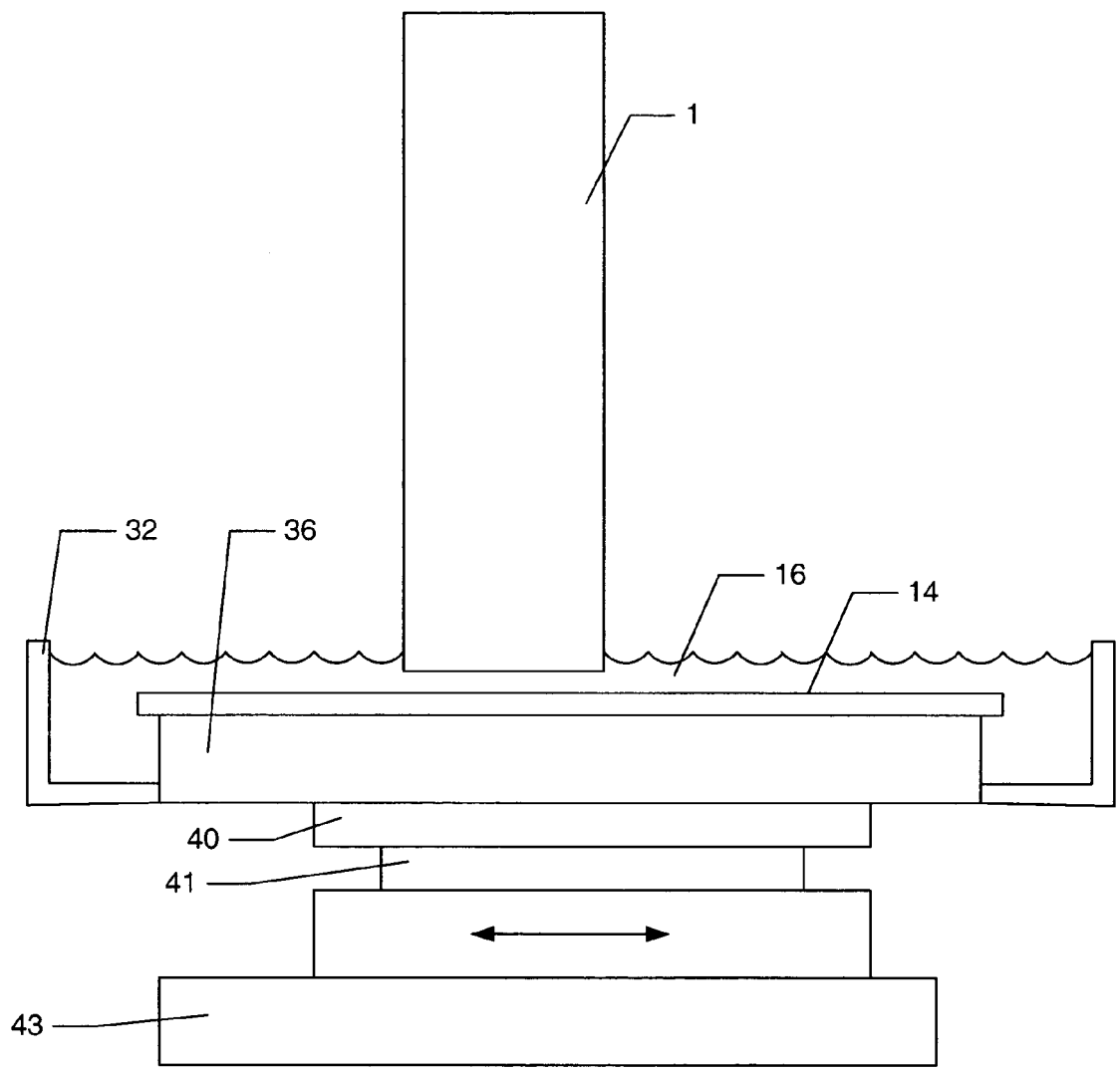
FIG. 6 is a schematic diagram illustrating a partial cross-sectional view of a system in which the immersion liquid is contained in a vessel.

FIG. 6 illustrates another embodiment of a containment system where immersion liquid is contained in vessel 32, which includes the space between inspection or review system 1 and specimen 14 under inspection or review. In this embodiment, the inspected specimen 14 supported on the stage or chuck moves with the immersion liquid relative to inspection or review system 1. Filtering and temperature control systems for the immersion liquid are not shown, but may be included. Containment vessel 32 can be expanded to include motion control stages 41, 42, 43, 44 and surface support or chuck 36 (not shown) where all motions take place in the liquid. Additionally, relative motion between specimen 14 under examination and the inspection or review system 1 may be imparted by moving the inspection system or review system and keeping the surface under examination fixed with the containment vessel as shown in either FIG. 5 or FIG. 4.

Figure 7:
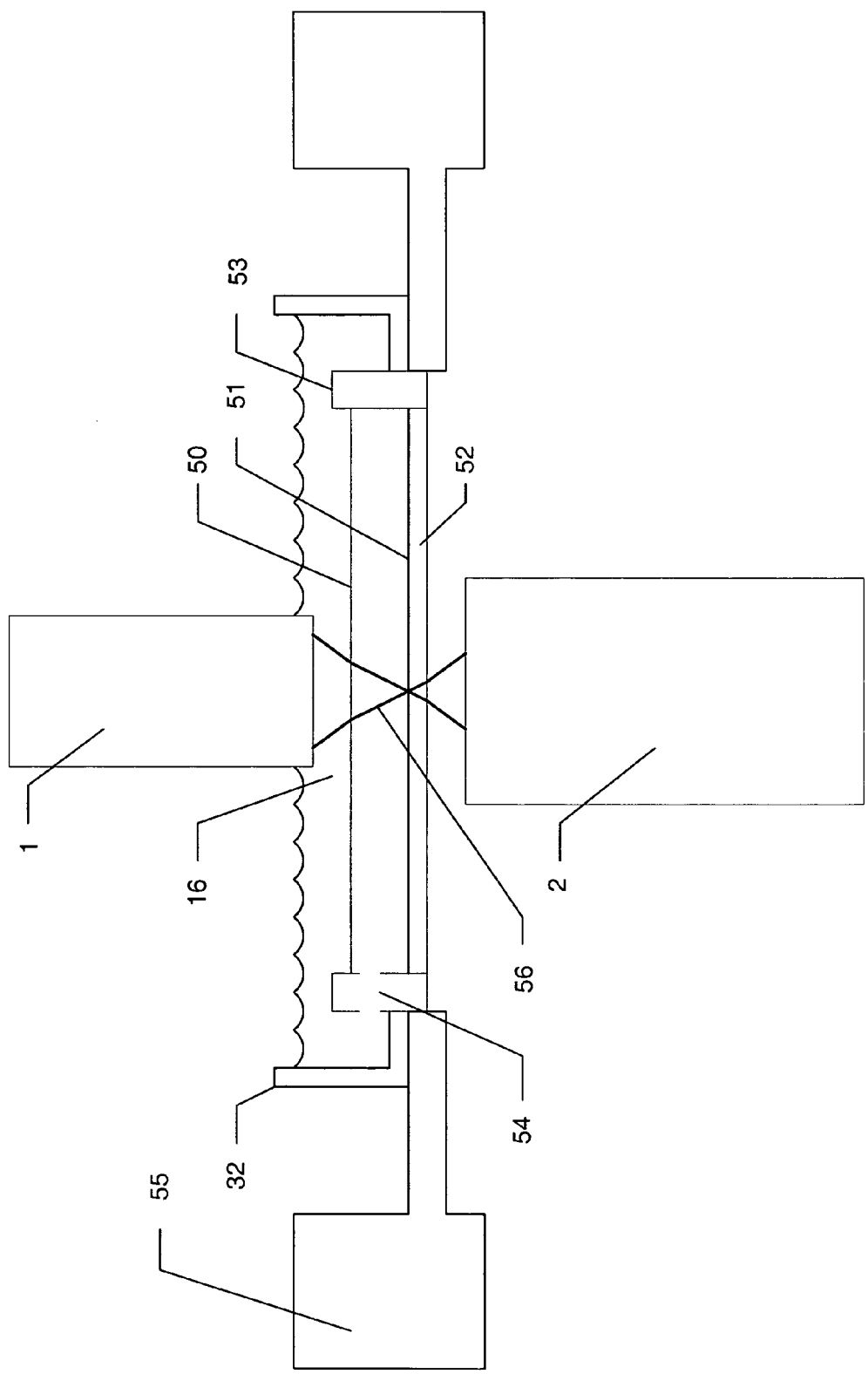
FIG. 7 is a schematic diagram illustrating a partial cross-sectional view of a system that can be used to inspect a reticle using an immersion liquid.

FIG. 7 illustrates another embodiment where a lithography mask, or reticle, is inspected in transmission with reticle inspection or review system 1 with illumination from the back side of the mask by illumination system 2. The illumination system illuminates the reticle surface 51 with illumination beam 56. Inspection or review system 1 is focused on the reticle surface. The mask is comprised of cell 53 holding reticle substrate 52 with reticle structures formed thereon and protected with pellicle 50. The mask is immersed in liquid 16 and liquid is allowed or pumped into a space between the pellicle and reticle through space 54 in the mask cell. Motion system 55 includes provisions for z, x, y, and theta motions for focus, alignment, and scanning the reticle relative to inspection or review system 1 and illumination system 2. This embodiment may include a re-circulating pump, filter and temperature control systems similar to those illustrated in FIG. 4, but not illustrated here. Alternate configurations are possible where the whole mask including the substrate and illumination system 2 are immersed in the liquid. Another embodiment is possible where scanning of the reticle is obtained by moving inspection or review system 1 and illumination system 2 relative to a fixed position of the mask.

In some embodiments, the inspection or review system may be configured to form an aerial image of the reticle (i.e., a two-dimensional image of the reticle) from the light transmitted by the reticle. For example, such an inspection or review system may be configured to image the light transmitted by the reticle onto a detector having a two-dimensional array of photosensitive elements such as photodiodes or a camera such as a charge-coupled device (CCD) camera or a time delay integration (TDI) camera. Such an inspection system may be referred to as an "aerial imaging reticle inspection system."

In alternative embodiments, illumination system 2 shown in FIG. 7 may be replaced with an additional inspection or review system that does not include an immersion lens. In such embodiments, the system may be configured to inspect two opposing sides of a specimen such as a wafer substantially simultaneously. In the case of a wafer, the surface of the specimen that is immersed in the liquid may be a frontside of the wafer. As such, the inspection or review system may detect smaller defects on this side of the wafer. The inspection or review system will have a lower resolution on the non-immersed side of the specimen. Therefore, in the case of a wafer, the non-immersed surface of the specimen may be a backside of the wafer since the resolution requirements for the backside of the wafer may be lower than the resolution requirements for the frontside of the wafer.

Figure 8:
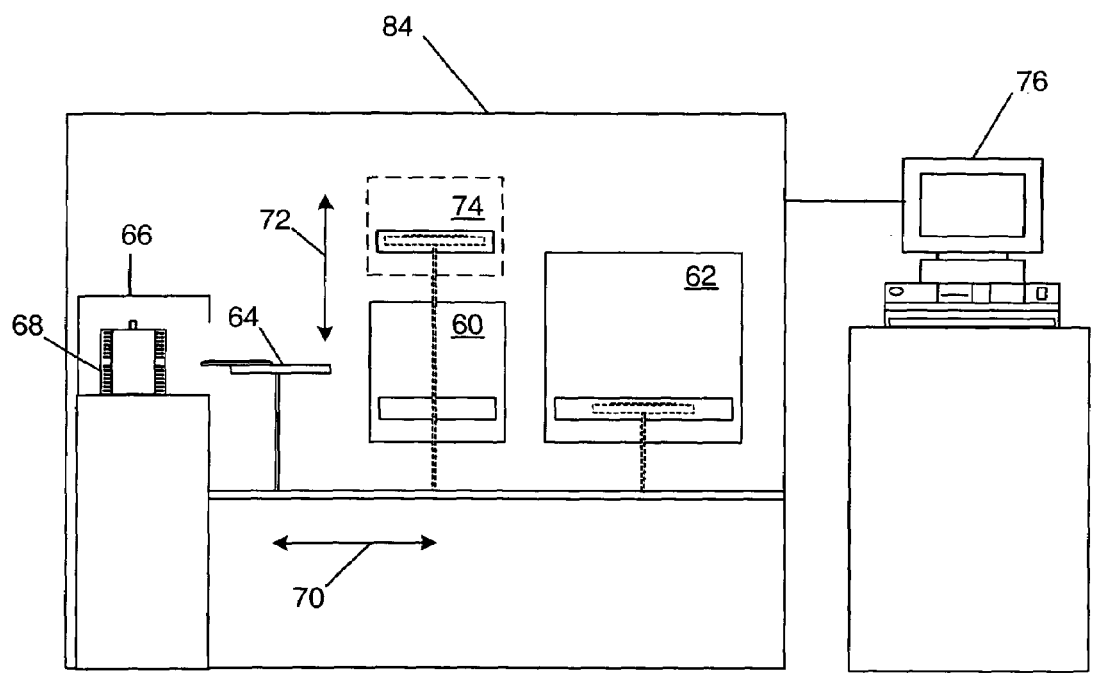
FIG. 8 is a schematic diagram illustrating a cross-sectional view of a system that includes an inspection or review subsystem and a processing subsystem.

FIG. 8 illustrates a further embodiment of an inspection or review system. In this embodiment, the inspection or review system includes inspection or review subsystem 60. The inspection or review subsystem may be configured as illustrated in FIGS. 1 and 4–7 and as described above. The inspection or review system illustrated in FIG. 8 also includes processing subsystem 62. Processing subsystem 62 may be configured to remove any residual liquid from the specimen after inspection or review. In this manner, the selected liquid may determine an appropriate configuration for processing subsystem. For example, in some embodiments, the processing subsystem may be configured to dry the specimen. Such a processing subsystem may be appropriate if a liquid such as water is used as the immersion liquid. Such a processing subsystem may be configured to dry wafers by spinning the wafers, by heating the wafers, or by flowing a gas over the specimen.

In some embodiments, the processing subsystem may be configured to clean the specimen after inspection or review. Such a processing subsystem may be appropriate if a liquid such as water and another liquid, water and a wetting agent, or a non-aqueous liquid is used as the immersion liquid. The processing subsystem may include any cleaning system known in the art of wafer or reticle cleaning. In either embodiment, the processing subsystem may be configured to remove substantially all of the liquid from the specimen. In addition, the liquid may be selected such that a residue is not present on the specimen after inspection, review, or post-inspection processing. In this manner, the inspection or review system may be configured as a "dry in/dry out" system in the sense that the specimen is dry both before and after inspection or review.

As shown in FIG. 8, the inspection or review system also includes handler 64. Handler 64 is configured to transfer the specimen from the inspection or review subsystem to the processing subsystem. In this manner, the system may be configured to automatically transfer the specimen to the processing subsystem after inspection or review. Therefore, the system may be configured as a "cluster tool." As shown in FIG. 8, the handler may be configured to move in one or more directions such as the direction indicated by vector 70 and the direction indicated by vector 72. The handler may include any mechanical or robotic device known in the art. In addition, the system may include more than one handler.

The inspection or review system may include a number of other components such as load module 66. Load module 66 may be configured to receive a specimen that is to be inspected or reviewed. For example, as shown in FIG. 8, in the case of wafers, the load module may be configured to receive cassette 68, which may include one or more wafers. The load module may also be configured to receive other specimen carriers such as front opening unified pods ("FOUP") or any other cassettes known in the art. In addition, load module 66 may be configured in a Standard Mechanical Interface ("SMIF") technique such that the load module may automatically receive cassettes from another system.

The inspection or review system may also include one or more additional subsystems 74. An additional subsystem may be an additional inspection or review subsystem, an additional processing subsystem, or a different review subsystem. Examples of other defect review tools include e-beam tools such as the ev300 available from KLA-Tencor and SEMVISION from Applied Materials, Inc. and optical tools like the CRS from KLA-Tencor and AIMS review station configured to inspect reticles available from Carl Zeiss, Inc. The inspection system may include any number of inspection subsystems, processing subsystems, and/or additional subsystems. The subsystems may be arranged in a variety of ways.

As shown in FIG. 8, the load module, the inspection or review subsystem, the processing subsystem, and optionally an additional subsystem may be arranged in unit 84. Environmental conditions within unit 84 may be controlled substantially independently from environmental conditions of the space surrounding the unit. For example, the environment within the unit may be controlled by chemical filtration of atmospheric air or by feeding a supply of sufficiently pure gas. In this manner, the environment within the unit may be controlled such that levels of chemical species including, but not limited to, ammonia and amine-group-containing compounds, water, carbon dioxide, and oxygen may be reduced. In addition, environmental conditions within the unit may be controlled by a processor, which may be coupled to the system and may be configured according to any of the embodiments described herein. For example, environmental conditions within unit 84 such as relative humidity, particulate count, and temperature may be controlled by the processor. Such a unit may be commonly referred to as a "mini-environment." The unit may also include a common handler as described above and a common power source shared by the various subsystems of the inspection system.

The inspection system may also include processor 76. Processor 76 may be coupled to at least inspection subsystem 60 and processing subsystem 62. Processor 76 may be configured to control various components of the system such as the handler, the inspection or review subsystem, and the processing subsystem. The processor may be configured to perform a number of other functions such as analyzing signals or data generated by the inspection or review subsystem. For example, the processor may analyze the signals or data to detect defects on a specimen. The processor may be further configured to generate output in response to the detected defects. The output may include information about the specimen such as, but not limited to, locations of defects and characteristics of defects. In addition, the output may include any output that may provide information about the specimen, defects on the specimen, the system, the inspection or review subsystem, or the processing subsystem to a user such as an operator, or a process engineer. The system may include a single processor coupled to one or more elements of the system, namely, an inspection or review subsystem and a processing subsystem. Alternatively, the system may include multiple processors (not shown).

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An inspection or review system, comprising:
   an optical component configured to project ultraviolet light onto a specimen during inspection or review of the specimen, wherein the specimen is a wafer or a reticle; and
   a liquid disposed between the optical component and the specimen during the inspection or the review, wherein the liquid is in contact with a surface of the optical component and a surface of the specimen, and wherein the liquid does not permanently alter properties of the optical component or properties of the specimen.

2. The system of claim 1, wherein the presence of the liquid between the optical component and the specimen increases resolution of the inspection or review system.

3. The system of claim 1, wherein the liquid has an index of refraction that is approximately equal to an index of refraction of the optical component.

4. The system of claim 1, wherein the liquid has an index of refraction that is different than an index of refraction of an upper layer formed on the specimen.

5. The system of claim 1, wherein the liquid occupies approximately an entire volume between the surfaces of the optical component and the specimen.

6. The system of claim 1, wherein the liquid occupies spaces between features on the specimen.

7. The system of claim 1, wherein air is not present between the surfaces of the optical component and the specimen.

8. The system of claim 1, wherein the liquid does not scatter the ultraviolet light.

9. The system of claim 1, wherein the liquid comprises water.

10. The system of claim 1, wherein a substantial portion of the liquid comprises water.

11. The system of claim 1, wherein the liquid comprises a wetting agent.

12. The system of claim 1, wherein the liquid can be removed from the surface of the specimen after inspection such that a residue is not present on the specimen after the inspection.

13. The system of claim 1, wherein the inspection or review comprises bright field inspection or review, dark field inspection or review, or dark field and bright field inspection or review.

14. The system of claim 1, wherein the system is configured as a confocal optical system.

15. The system of claim 1, wherein the system is configured to scan the specimen while the liquid is disposed between the surfaces of the optical component and the specimen.

16. The system of claim 1, wherein the system is configured to generate flow of the liquid between the surfaces of the optical component and the specimen during the inspection or review.

17. An inspection or review system, comprising:
   an inspection or review subsystem configured to project ultraviolet light through an optical component, a liquid, and onto a specimen, wherein the liquid contacts the optical component and the specimen, and wherein the specimen is a wafer or a reticle; and
   a processing subsystem configured to remove the liquid from the specimen after inspection or review.

18. The system of claim 17, wherein the processing subsystem is further configured to clean the specimen after the inspection or review.

19. The system of claim 17, wherein the processing subsystem is further configured to remove substantially all of the liquid from the specimen.

20. The system of claim 17, further comprising a handler configured to transfer the specimen from the inspection or review subsystem to the processing subsystem.

* * * * *